United States Patent
Wei

(10) Patent No.: US 8,516,908 B2
(45) Date of Patent: Aug. 27, 2013

(54) SAMPLE SYSTEM FOR GASEOUS EMISSION MEASUREMENT

(75) Inventor: Qiang Wei, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 212 days.

(21) Appl. No.: 13/180,941

(22) Filed: Jul. 12, 2011

(65) Prior Publication Data

US 2013/0014560 A1 Jan. 17, 2013

(51) Int. Cl.
*G01N 1/24* (2006.01)

(52) U.S. Cl.
USPC ......................................................... 73/863.03

(58) Field of Classification Search
None
See application file for complete search history.

(56) References Cited

U.S. PATENT DOCUMENTS

| | | | |
|---|---|---|---|
| 3,653,399 A | 4/1972 | Steele | |
| 5,627,328 A | 5/1997 | Sheridan et al. | |
| H001757 H | 11/1998 | Seltzer | |
| 6,959,590 B2 | 11/2005 | Hendren | |
| 7,389,703 B2 | 6/2008 | Wei et al. | |
| 2003/0136177 A1 | 7/2003 | Hendren | |
| 2007/0068236 A1 | 3/2007 | Wei et al. | |
| 2007/0251307 A1 | 11/2007 | Graze, Jr. | |
| 2010/0005782 A1 | 1/2010 | Foster et al. | |
| 2010/0101302 A1 | 4/2010 | Graze, Jr. | |
| 2010/0310765 A1* | 12/2010 | Olsson et al. | 427/207.1 |

FOREIGN PATENT DOCUMENTS

| | | |
|---|---|---|
| EP | 1285267 | 6/2006 |
| WO | 0190741 | 11/2001 |
| WO | 2010048196 | 4/2010 |

* cited by examiner

*Primary Examiner* — Robert R Raevis
(74) *Attorney, Agent, or Firm* — Grossman, Tucker et al

(57) ABSTRACT

Disclosed herein are sampling systems and sampling methods for regulating the provision of sample gases to downstream analytical equipment, such as an exhaust bench for analyzing exhaust gases emitted from an internal combustion engine. In some embodiments, the described systems and methods can enable accurate measurements to be taken from a source of gaseous samples, regardless of the gaseous sample inlet pressure.

20 Claims, 6 Drawing Sheets

SAMPLE SYSTEM FOR GASEOUS EMISSION MEASUREMENT

BACKGROUND

Environmental protection agencies in many countries have enacted strict regulations for diesel exhaust particulate matter (PM) and NOx emissions. With current technologies, it is difficult to meet such regulations unless diesel particulate filter (DPF) and NOx reduction devices are installed in a vehicle exhaust system. Thus, significantly more complex exhaust systems have been installed in diesel vehicles manufactured in 2007 or later. For a typical heavy-duty diesel truck to meet 2010 US emission standards, exhaust aftertreatment devices, such as a diesel oxidation catalyst (DOC), a DPF, and a selective catalytic reduction (SCR) catalyst with urea injection or a NOx adsorber may be installed.

A DPF removes diesel particulate matter based on a filtration mechanism. Thus, while exhaust gas moves through the DPF, particulate matter is removed from the exhaust gas and stored in the filter. Over time the passage of exhaust gas through the pores of a DPF is progressively blocked, and the pressure required to maintain the exhaust gas flow increases. This pressure, which is the pressure higher than the exhaust must work against, is called "back pressure."

As a DPF operates it removes particulate from exhaust gas, and back pressure in the exhaust system increases. As the DPF is increasingly soiled, the back pressure will eventually increase to a point significantly greater than the back pressure of a clean DPF, particularly if pressure measurements are taken upstream of the DPF. Beyond a certain limit, excess back pressure can increase exhaust temperature, carbon monoxide emission, and PM.

Because of the detrimental effects of excessive exhaust back pressure on an engine, DPF's are periodically regenerated by removing trapped particulate matter. By regenerating a DPF loaded with soot, the back pressure in an exhaust system can be reduced to a normal level.

To study and evaluate the performance of engines and aftertreatment devices, engineers and researchers are interested in measuring gaseous emissions (CO, THC, NOx, $CO_2$, etc.) under the varying back pressure conditions observed when a DPF is used in an exhaust system. However, the environmental conditions present in exhaust systems using a DPF present several problems for conventional gas analyzers and emissions benches, as discussed below.

For the purpose of the present disclosure, the term "emissions bench" refers to instrumentation that is configured to analyze one or more properties of exhaust gases generated by a combustion source, such as an internal combustion engine. For example, an emissions bench may include one or more instruments configured to measure or determine at least one of the identity, mass, and concentration of one or more components (e.g., $O_2$, $CO_2$, CO, $NO_R$, and hydrocarbons) of such exhaust gases.

Conventional gas analyzers and emission benches are generally designed to operate in a low back pressure environment, such as in the range of 0 to 30 kPa above ambient air pressure. Once the back pressure exceeds 30 kPa above ambient air pressure or drops below ambient air pressure, the sample flow into the instrument may be beyond the control of the sampling system used to provide samples of the exhaust gas to a gaseous analyzer or emissions bench. This can lead to improper operation of the gaseous analyzer and other instruments in an emissions bench.

FIG. 1 is a schematic of a conventional gaseous measurement system utilized in exhaust emission measurement. As shown, system 100 includes a probe 103 disposed within tailpipe 101 of a vehicle. Probe 103 samples exhaust 102 flowing through tailpipe 101. The resulting sample is pulled through particulate filter 104 (e.g., a high efficiency particulate air filter) via sample line 105 and vacuum pump 106, and ultimately enters emissions bench 107.

While the system shown in FIG. 1 is effective in some circumstances for analyzing exhaust, the sample flow rate may be sensitive to the inlet pressure. If the inlet pressure to the probe 103 is outside of the design inlet pressure for the system, the sample flow rate may be out of the designed sample flow rate. As a result, the instruments within emissions bench 107 may not operate correctly.

To address this issue, several modification kits have been developed. One example of such modification utilizes a bypass to lower the sample inlet flow to the analyzing instruments when a high back pressure is detected. That is, when a high back pressure condition is detected, the system maintains the inlet pressure within a designed range by increasing a bypass flow upstream of the emission bench.

While the use of a bypass can address the pressure problem encountered during a high back pressure condition, the bypass impacts the residence time of a sample flowing through the system. Specifically, as back pressure increases, sample residence time decreases because more of the sample flow is vented through the bypass, e.g., via a bypass pump. In contrast, sample residence time increases under a lower back pressure condition. Due to this variance, the residence time of the sample may not correlate with a delay time that is stored in the emissions bench. This can bias the results of measurements taken with instrumentation within emissions bench 107, and may cause other measurement errors.

SUMMARY

One aspect of the present disclosure relates to sampling systems, including sampling systems that are useful in the measurement of various characteristics of exhaust gases. In non-limiting embodiments, the sampling systems include a system inlet for receiving a gaseous sample, a pressure regulator coupled to the system inlet, and a pump coupled downstream of the pressure regulator. The systems further include a pressure monitor configured to receive the gaseous sample downstream of the system inlet, a proportional valve coupled downstream of the pressure monitor, and a controller coupled to the pressure monitor and the proportional valve. In operation, the pressure monitor is configured to measure a pressure differential of the gaseous sample as it flows through the pressure monitor, and to output a first pressure differential signal corresponding to a first gas flow rate to the controller. The controller is configured to compare the first pressure differential signal to a second pressure differential signal corresponding to a second gas flow rate, and to drive the proportional valve open or closed so as to adjust the first gas flow rate to the second gas flow rate.

Also disclosed herein are methods for operating sampling systems in accordance with the present disclosure. In some embodiments, the methods include providing a gas sampling system that includes a system inlet for receiving a gaseous sample at an inlet pressure; a pressure regulator coupled to the system inlet; a pump coupled downstream of the pressure regulator; a pressure monitor configured to receive the gaseous sample downstream of the system inlet; a proportional valve coupled downstream of the pressure monitor; and a controller coupled to the pressure monitor and the proportional valve. The methods further include supplying a gaseous sample to the pressure monitor at a first gas flow rate and measuring a pressure differential of the gaseous sample as it flows through the pressure monitor. Such methods may further include providing a first pressure differential signal corresponding to the pressure differential to at least one controller, and comparing the first pressure differential signal to a second pressure differential signal corresponding to a second gas flow with the at least one controller. In addition, the methods may further include outputting a signal from the at least one controller to drive the proportional valve open or closed, thereby adjusting the first gas flow rate to the second gas flow rate.

BRIEF DESCRIPTION OF THE DRAWINGS

The accompanying drawings, which are incorporated in and constitute a part of this specification, illustrate several non-limiting embodiments of the present disclosure and, together with the description, serve to explain the principles of the present disclosure.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

One aspect of the present disclosure relates to sampling systems, including sampling systems for use in analyzing exhaust gases emitted from an internal combustion engine. In some embodiments, such systems can enable accurate measurements to be taken from a source of gaseous samples, regardless of the gaseous sample inlet pressure.

Figure 1:
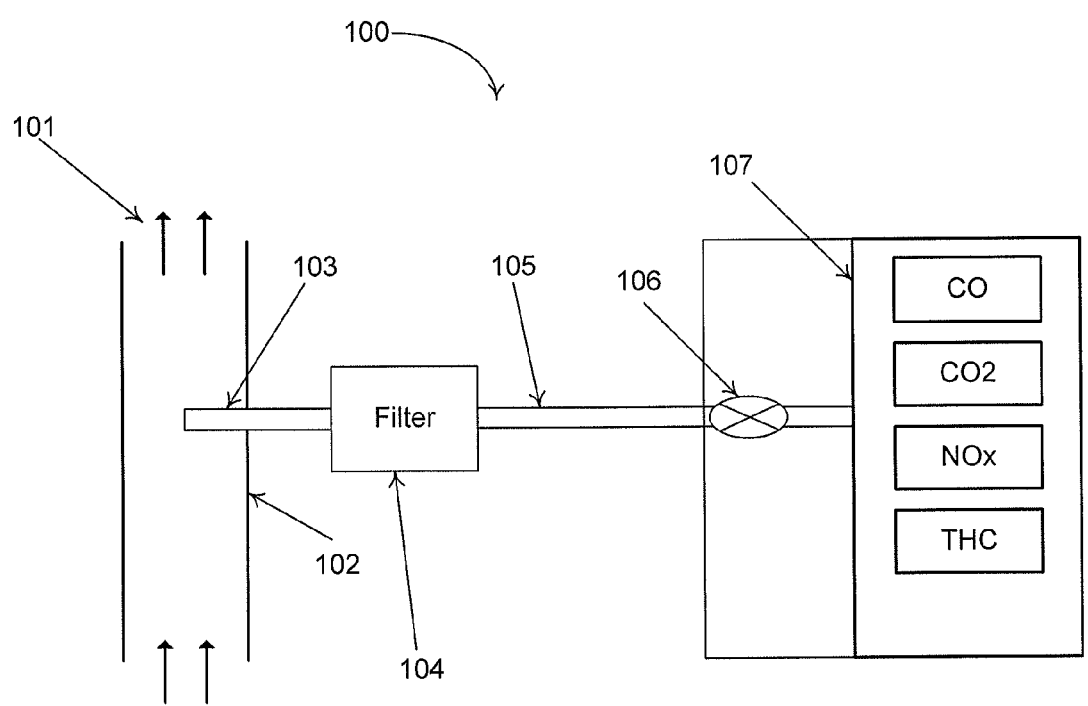
FIG. 1 illustrates a gaseous emission measurement system in accordance with the prior art.
Figure 2:
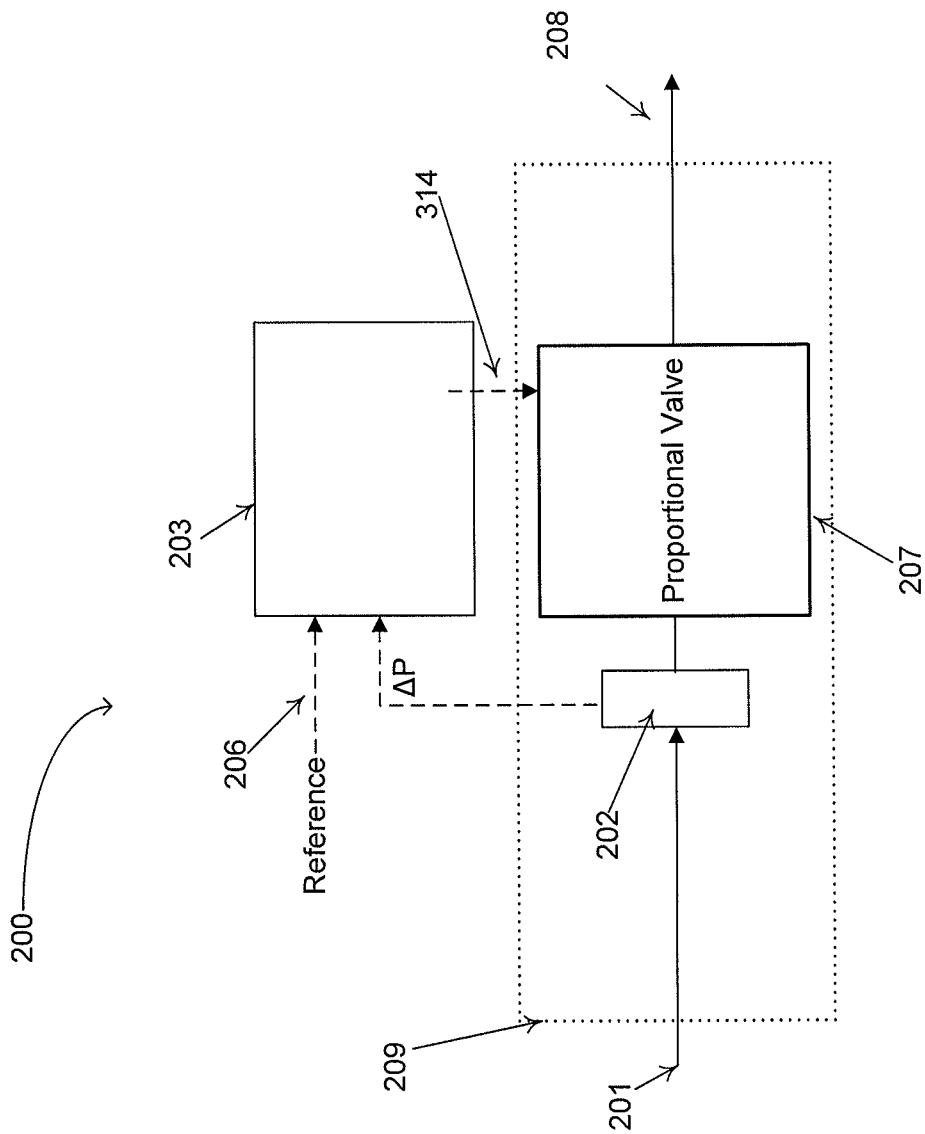
FIG. 2 illustrates a first portion of the sampling system in accordance with the present disclosure.

In this regard, reference is made to FIG. 2, which depicts a non-limiting example of a first portion of the overall sampling system (see FIGS. 4 and 5) in accordance with the present disclosure. As shown, sampling system 200 includes a system inlet 201, a pressure monitor 202, a proportional valve 207, and a system outlet 208. In this example, a sample gas flow enters sampling system 200 via system inlet 201, flows through pressure monitor 202, through proportional valve 207, and ultimately through system outlet 208.

System inlet 201 is generally configured to receive a sample gas flow from a source, such as the exhaust gas of an engine, and to convey that sample gas flow to other components of sampling system 200. In this regard, system inlet 201 may be configured as a probe, an open tube, or another structure suitable for receiving a sample gas flow. In operation, system inlet 201 is connected to or disposed within a source of a sample gas. Non-limiting examples of such sources include ambient air, exhaust from an internal combustion engine, exhaust from a power plant, a canister, and a syringe. In some embodiments, system inlet 201 is connected to or disposed within the exhaust gas of a diesel engine. For example, system inlet 201 may be connected to the exhaust pipe of a diesel engine, such that at least a portion of the exhaust flowing through the exhaust pipe enters sampling system 200 via system inlet 201.

Once a sample gas flow enters system inlet 201, it is conveyed to other components of sampling system 200. In the non-limiting example shown in FIG. 2, the sample gas flows directly from system inlet 201 to pressure monitor 202. Generally, pressure monitor 202 is configured so as to incite a pressure differential in the sample gas flow. As used herein, the phrase "incite a pressure differential" means that pressure monitor 202 creates a measurable pressure difference in a gas flow (e.g., a sample gas flow or a flow of calibration gas).

As the sample gas flow passes through pressure monitor 202, the pressure differential is measured by pressure monitor 202, which then outputs a pressure differential signal (shown in FIGS. 2-5 as "$\Delta P$") to controller 203. In some embodiments, the pressure differential signal correlates to the flow rate of the sample gas flow as it passes through pressure monitor 202.

Controller 203 compares the measured pressure differential signal to reference pressure differential signal 206, or set point, which may be stored in a memory of controller 203. Generally, reference pressure differential signal 206 correlates to a reference gas flow rate, which may be the same or different from the gas flow rate of the sample gas flow passing through pressure monitor 202. If the measured pressure differential signal differs from reference pressure differential signal 206, controller 203 communicates with proportional valve 207, and drives proportional valve further open or closed so as to adjust the sample gas flow rate to the reference gas flow rate.

Proportional valve 207 is an electrically controlled, variably acting valve. Generally, this means that the size of the opening in proportional valve 207 through which gas/material can pass is controlled in response to an electronic signal. In this way, proportional valve 207 controls the amount and rate of material that passes through it. It should be noted that while the present disclosure repeatedly describes the use of a proportional valve, other types of variably active valves may also be used. For example, a servovalve or a servo-proportional valve or a mass flow controller or a volume flow controller may be used instead of or in addition to proportional valve 207.

As noted above, controller 203 communicates with proportional valve 207, and drives proportional valve 207 further open or closed based on the difference between the measured pressure differential signal of the sample gas and reference pressure differential signal 206. If the measured pressure differential signal is lower than reference pressure differential signal 206, controller 203 drives proportional valve 207 further open, so as to adjust the sample gas flow rate to the reference gas flow rate. If the measured pressure differential signal is higher than reference pressure differential signal 206, controller 203 drives proportional valve 207 further closed, so as to adjust the sample gas flow rate to the reference gas flow rate. In this way, the flow rate of the sample gas exiting system outlet 208 is maintained at constant value, e.g., corresponding to the reference gas flow rate, regardless of the inlet pressure of the sample gas flow at system inlet 201.

The sample gas flow exiting system outlet 208 may be input to a variety of downstream systems and instrumentation, such as spectrometers, particulate analyzers, and chromatographs. In some embodiments, the sample gas flow from system outlet 208 is input to an emissions bench. Such emissions bench may contain equipment for analyzing characteristics of the sample gas flow, such as CO content, total hydrocarbon content, NOx content, and $CO_2$ content.

All or a portion of the components of sampling system 200 may be disposed within an enclosure. This concept is illustrated in FIGS. 2-5, wherein various components of sampling system 200 are present within enclosure 209. In some embodiments, enclosure 209 is a heated enclosure. In such embodiments, enclosure 209 may heat the components disposed therein to a temperature above the condensation temperature of the components of the sample gas flowing through sampling system 200. For example, where system inlet is connected to a source of exhaust gas from a diesel engine, the temperature of enclosure 209 may be controlled to temperatures up to 191° C. or higher. In this way, enclosure 209 can limit or prevent condensation, of water, hydrocarbons, and/or other materials within sampling system 200.

In some embodiments, the source of sample gas may be laden with impurities such as particulate matter. Indeed, the presence of particulate matter is expected when the sample gas originates or is derived from a combustion source, such as an internal combustion engine or a power plant. To prevent sampling system 200 from becoming contaminated with such particulate matter, a filter may be installed upstream of system inlet 201 or between system inlet 201 and downstream components. For example, a high efficiency particulate air filter or a small diesel particulate filter (DPF) may be installed upstream of system inlet 201, so as to remove at least a portion of the particulate from the sample gas before it enters sampling system 200. The filter may be disposed within enclosure 209, and may be heated (independently or within enclosure 209) for the same reasons noted above with respect to the heating of other components of sampling system 200.

Pressure monitor 202 may have any configuration suitable for inciting a pressure differential in a gas flow, and measuring that pressure differential. For example, pressure monitor 202 may be configured to include at least one of an orifice flow meter, a nozzle flow meter, and a venturi flow meter, the construction and operation of which will be understood by one of ordinary skill in the art.

Figure 3:
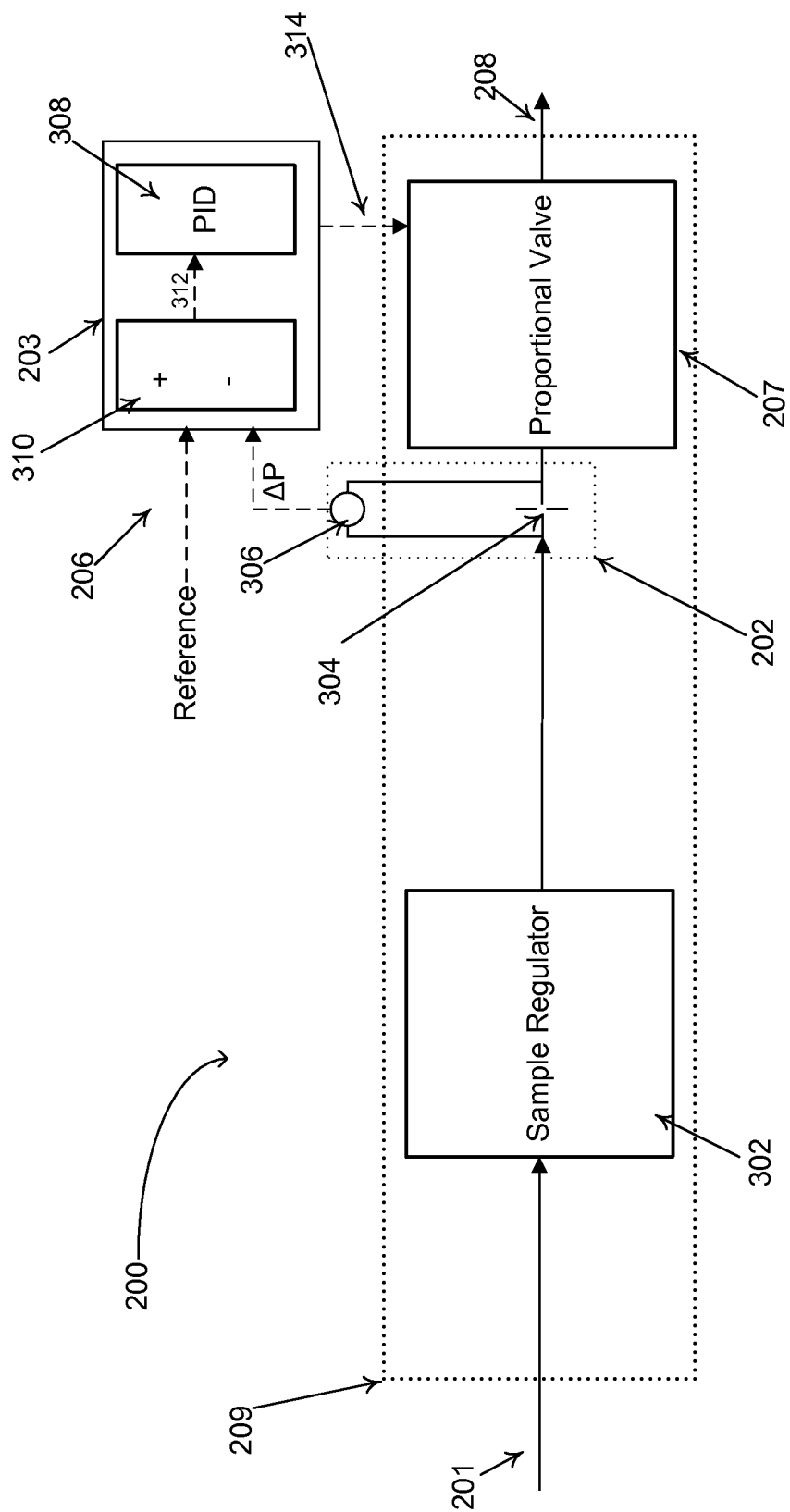
FIG. 3 illustrates another portion of the sampling system in accordance with the present disclosure.
Figure 4:
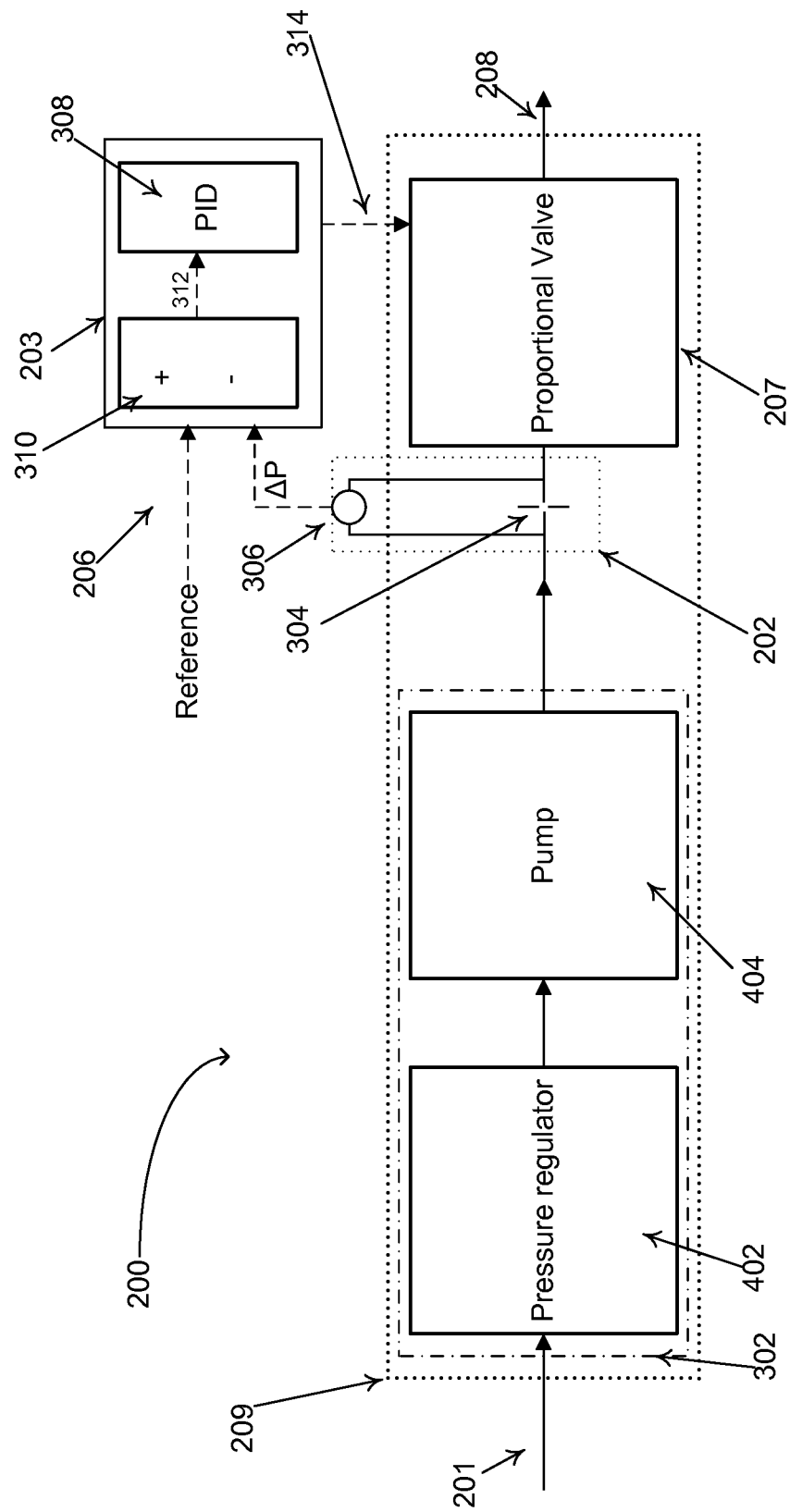
FIG. 4 illustrates a non-limiting example of a sampling system in accordance with the present disclosure.
Figure 5:
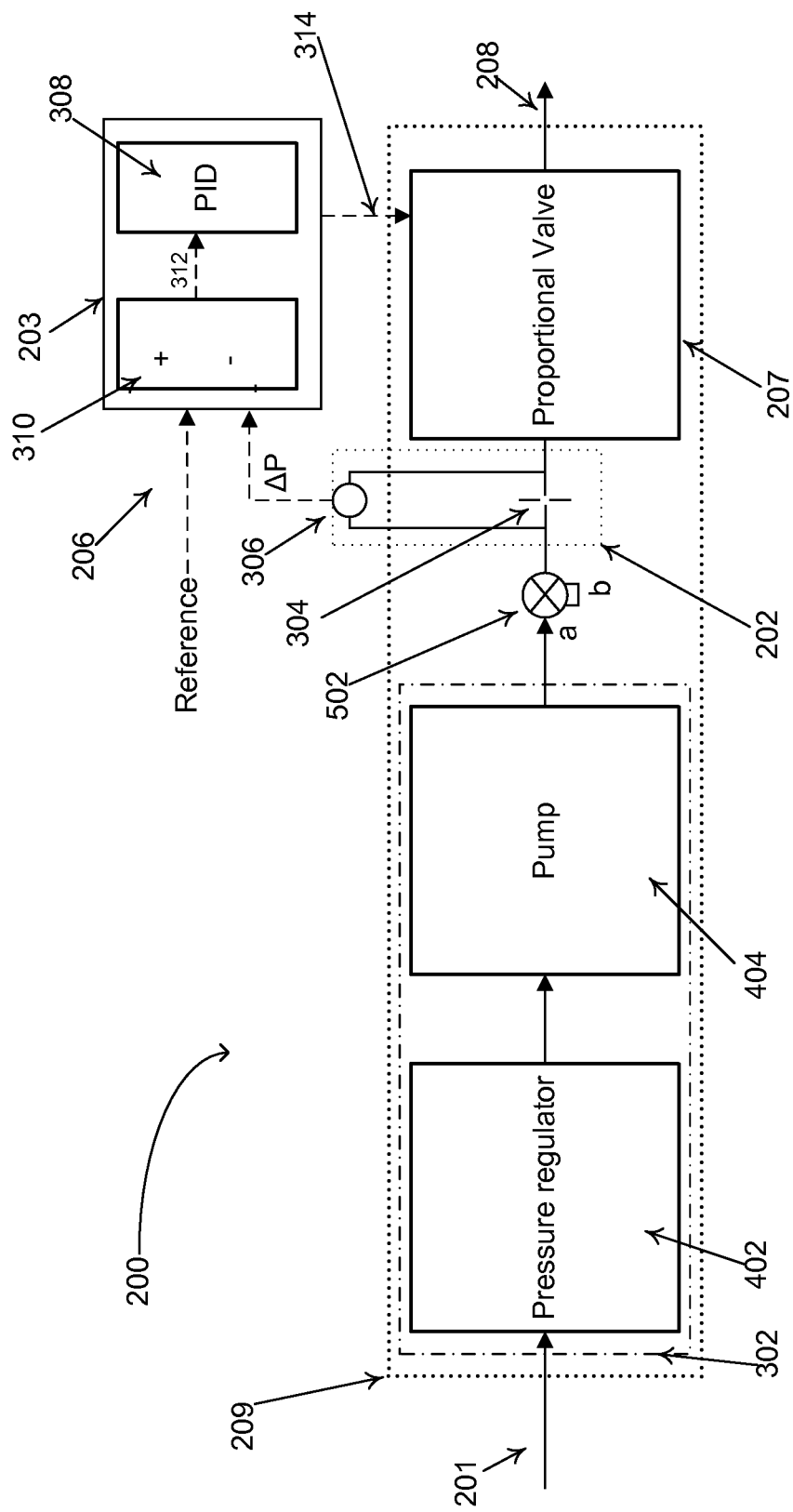
FIG. 5 illustrates a non-limiting example of a sampling system in accordance with the present disclosure.

In some embodiments, pressure monitor 202 is configured as an orifice flow meter. This concept is illustrated in FIGS. 3-5, wherein pressure monitor 202 includes orifice 304. When a sample gas flow encounters orifice 304, the pressure on one side of orifice 304 differs from the pressure on the other side of orifice 304. This pressure differential can be measured, e.g., with differential pressure transducer 306. Of course, pressure monitor 202 may be configured to include other components, such as one or more thermocouples, absolute pressure transducers, and differential pressure transducers. Of note is the fact that when the sample gas flow rate changes, the pressure difference measured by pressure monitor 202 changes as well. In the non-limiting examples shown in FIGS. 3-5, the change in sample gas flow rate is reflected by the magnitude of the difference between the pressure on the inlet and outlet sides of orifice 304.

Controller 203 may be of any configuration suitable for comparing a pressure differential signal corresponding to the measured pressure differential of a sample gas to a reference pressure differential signal, as noted above. For example, controller 203 may be configured as a feedback controller such as a proportional, integral, derivative (PID) controller.

This concept is illustrated in FIGS. 3-5, wherein controller 203 includes summer 310 and PID loop 308. Summer 310 receives a reference pressure differential signal 206 (e.g., from a memory of controller 203) at its positive input. Summer 310 further receives the measured pressure differential signal transmitted by pressure monitor 202 at its negative input. Summer 310 is a summing operational amplifier that is configured to add two signals together. In the example shown in FIGS. 3-5, summer 310 is configured to add the reference pressure differential signal 206 and the measured pressure differential signal, so as to produce error signal 312. Typically, one of the inputs to summer 310 is a negative value and thus, error signal 312 corresponds to a difference between the measured pressure differential signal and reference pressure differential signal 206. Error signal 312 is then processed by PID loop 308 to produce control signal 314. In response to control signal 314, proportional valve 207 is driven further open or closed so as to adjust the sample gas flow rate (corresponding to the measured pressure differential signal) to the reference gas flow rate (corresponding to the reference pressure differential signal).

Reference pressure differential signal 206 may be manually inputted to controller 203, or it may be derived by a calibration measurement performed using a source of calibration gas. In the latter case, a source of calibration gas is connected to sampling system 200, and is allowed to flow through pressure monitor 202. As with the sample gas flow, the pressure monitor 202 induces a pressure differential in the flow of calibration gas. The pressure monitor measures this pressure differential, and outputs reference pressure differential signal 206 to controller 203. Reference pressure differential signal 206 may be stored in a memory of controller 203, and is used in the performance of controller 203's functions, as described previously.

The calibration gas may be any source of gas that is suitable for generating a reference pressure differential signal. Non-limiting examples of calibration gas include ambient air, $CO_2$, He, Ar, Kr, $N_2$, $O_2$, and Xe. In some embodiments, the calibration gas is ambient air.

Reference pressure differential signal 206 (and its associated flow rate) may be used to calibrate certain parameters of analytical instrumentation connected downstream of system outlet 208. For example, the reference pressure differential signal may be used to calibrate the expected sample residence time in such instrumentation. Because controller 203 operates to control the flow rate of the sample gas exiting system outlet 208 to the reference gas flow rate, using reference pressure differential signal 206 to calibrate downstream instrumentation can result in even further improvements to the measurement accuracy of such instrumentation. This is because the residence time of the sample gas flow in the downstream analytical instruments may not fluctuate in response to the sample gas pressure at system inlet 201 (i.e., the inlet pressure of the sample gas). Indeed, in some cases the residence time of the sample gas flow in downstream analytical instrumentation does not fluctuate in response to the inlet pressure of the sample gas.

The inlet pressure of the sample gas flow of the present disclosure (i.e., the pressure at system inlet 201 in FIGS. 4 and 5) may now vary over a wide range. For example, the inlet pressure may range from about 30 kPa (or less) below ambient pressure to about 1000 kPa (or more) above ambient pressure. Accordingly, the present disclosure contemplates inlet pressures to sampling systems that preferably range from about −30 kPa to about 1000 kPa. In some embodiments, the inlet pressure correlates to the back pressure present in the exhaust system of an engine, such as a diesel engine. Therefore, the systems and methods of the present disclosure now provide for the accurate measurement of various characteristics of the sample gas regardless of the inlet pressure, by maintaining the outlet gas flow rate at a substantially constant value corresponding to a reference gas flow rate.

The ability of the systems and methods described herein to control sample gas flow rate exiting system outlet 208 can be particularly useful in the context of an emissions measurement system. In such a system, an emissions bench measures the characteristics of an exhaust gas, such as the exhaust of a diesel engine. As noted above, the exhaust pressure of a diesel engine can vary widely, e.g., from about 30 kPa below ambient pressure to about 1000 kPa above ambient pressure. Left unchecked, the variation inlet pressure may cause an emissions bench to make inaccurate measurements because the residence time of the sample gas could fluctuate in response to changes in exhaust pressure. If sampling system 200 is used to connect the exhaust gas source to the emissions bench, the sample gas flow rate exiting system exit 208 can remain substantially constant, e.g., at or about the flow rate of a calibration gas. In this way, the systems and methods of the present disclosure can allow the emissions bench to make accurate measurements, regardless of whether a source of exhaust gas is under a vacuum or high pressure condition.

In some instances, the pressure of the sample gas at system inlet 201 may be very high or very low. In such instances, actuation of the opening of proportional valve 207 may be insufficient to regulate the flow rate of the sample gas exiting system exit 208 to a reference gas flow rate. For example, in circumstances where the inlet pressure of the sample gas is high, proportional valve 207 may not be able to reduce the flow rate of the sample gas to the reference gas flow rate, even if it is in an almost fully closed position. Conversely, in circumstances where the inlet pressure of the sample gas is low or under a vacuum, the flow rate of the sample gas exiting system exit 208 may be below the reference gas flow rate, even if proportional valve 207 is in a fully open position.

To address these circumstances, the systems of the present disclosure may further include a sample regulator 302 coupled downstream of system inlet and upstream of pressure monitor 202. Generally, sample regulator 302 operates to control the pressure of the sample gas flow to a value that enables proportional control valve 207 to perform its aforementioned functions.

Sample regulator 302 may be of any configuration than enables the provision of a sample gas flow to pressure monitor 202 at a suitable pressure. As a non-limiting example of such a sample regulator, reference is made to FIGS. 4 and 5, wherein sample regulator 302 includes pressure regulator 402 and pump 404.

It should be noted that while a combination of pressure regulator 402 and pump 404 are shown in FIGS. 4 and 5, such components may be used separately. Moreover, while FIGS. 4 and 5 depict pressure regulator 402 and pump 404 connected in series, with pump 404 downstream of pressure regulator 402, other configurations may also be used. For example, pump 404 and pressure regulator 402 may be used in parallel. In such embodiments, system inlet 201 may be divided into two separate flows, one to pressure regulator 402, and the other to pump 404. Depending on the pressure condition of the source of sample gas to which system inlet is connected, the flow may be directed to pump 404 or to pressure regulator 402, as necessary.

Pressure regulator 402 may have any configuration suitable for receiving a sample gas flow at an inlet pressure, and outputting a sample gas flow at a set outlet pressure that is suitable for downstream components of sampling system 200. In the non-limiting examples shown in FIGS. 4 and 5, pressure regulator 402 has an outlet pressure suitable for input into pump 404, e.g., about 20 kPa or 50 kPa. In some embodiments, pressure regulator 402 is a high temperature pressure regulator capable of operating at temperatures greater than or equal to about 100° C., 150° C., 191° C., or more. Pressure regulator 402 may also be configured as a high pressure regulator that is capable of receiving sample gas at inlet pressures of up to 1000 kPa or higher.

When the inlet pressure of the sample gas is too low, actuation of proportional valve 207 may be insufficient to raise the sample gas flow to a reference gas flow, even if proportional valve 207 is fully open. In such instances, pump 404 can operate to increase the sample gas pressure, thereby allowing the sample gas flow rate to be controlled downstream to a reference gas flow rate. Pump 404 may have any configuration suitable for performing this function. In some embodiments, pump 404 is a vacuum pump, such as a leak-free vacuum pump. Like pressure regulator 402, pump 404 may be configured to withstand operation at high temperature, such as greater than or equal to about 100° C., 150° C., 191° C., or more.

With reference to FIGS. 4 and 5, there may be instances wherein, due to the source of the sample gas or the pressure drop across pressure regulator 402, the inlet pressure of the sample gas is less than the outlet pressure of pressure regulator 402. In such instances, sample gas may not flow through pressure regulator 402 to downstream components, or will flow at a pressure lower than the inlet pressure of the sample gas. In such instances, pump 404 can operate to raise the pressure of the sample gas exiting pressure regulator 402, by drawing additional sample gas from the source. Indeed, in circumstance where pump 404 is configured as a vacuum pump, such as a high temperature leak free vacuum pump, pump 404 may be capable of drawing sample gas flow from low pressure environments such as a vacuum condition. As a result, pump 404 is able to supply sample gas flow to downstream components of the sampling system and, ultimately to analytical instrumentation coupled system outlet 208, even under low inlet pressure conditions.

The sampling systems of the present disclosure may include a directional control valve, e.g., to facilitate the measurement of the sample gas pressure differential signals and reference pressure differential signals previously described. This concept is illustrated in FIG. 5, wherein solenoid 502 is connected downstream of sample regulator 302. As shown, solenoid 502 is a three-way solenoid having two inlets, a and b, and one outlet. Inlet a and inlet b may be connected to different gas sources. For example, inlet a may be connected to the source of sample gas flow, e.g., by connecting inlet a to an outlet of sample regulator 302, or by connecting inlet a directly to system inlet 201. Inlet b may be connected to a source of a calibration gas, such as ambient air or the other calibration gases discussed above. In this way, solenoid 502 can enable rapid switching between gas sources. As will be described in detail below, this functionality can be useful in the control of proportional valve 207, and in the calibration of instrumentation downstream of proportional valve 207.

While the non-limiting examples shown in FIG. 5 depict solenoid 502 as a three-way solenoid, it should be understood that other types of directional control valves may also be used. For example, solenoid 502 may be configured as a pneumatic directional control valve, a hydraulic directional control valve, or a manual directional control valve.

It should be further understood that the sampling systems described herein may be configured without solenoid 502, e.g., as shown in FIGS. 2, 3, and 4. In such instances, sampling system 200 may measure a reference pressure differential signal by connecting sampling system 200 to a source of calibration gas upstream of pressure monitor 202. For example, and with references to FIG. 2, sampling system 200 may be connected to a source of calibration gas by disconnecting system inlet 201 from a source of sample gas, and reconnecting it to a source of calibration gas. Alternatively, and with reference to FIG. 3, connection to a calibration gas source may be achieved by disconnecting the gas line between pressure monitor 202 and sample regulator 302 at the outlet of sample regulator 302, and reconnecting that gas line to a source of calibration gas. In either case, once a reference pressure differential signal has been measured using the calibration gas, sampling system 200 may be reconnected to a source of sample gas, and operated as explained above.

The components of sampling system 200 may also be configured to withstand high temperatures. Indeed, all or a portion of a system inlet 201, sample regulator 302, pressure monitor 202, proportional valve 207, solenoid 502, and controller 203 may be configured as "high temperature" components capable of withstanding temperatures ranging from about 100° C. to about 350° C., such as about 191° C. to about 350° C. In some embodiments, system inlet 201 is connected to a source of high temperature gas, such as exhaust gas from a diesel engine, and all or a portion of the components of sampling system 200 are configured to withstand temperatures ranging from about 191° C. to about 350° C.

Another aspect of the present disclosure relates to methods for sampling gases from a gaseous source, such as the exhaust stream of an internal combustion engine. In this regard, reference is made to FIG. 6, which provides a flow diagram of a non-limiting method in accordance with the present disclosure.

Figure 6:
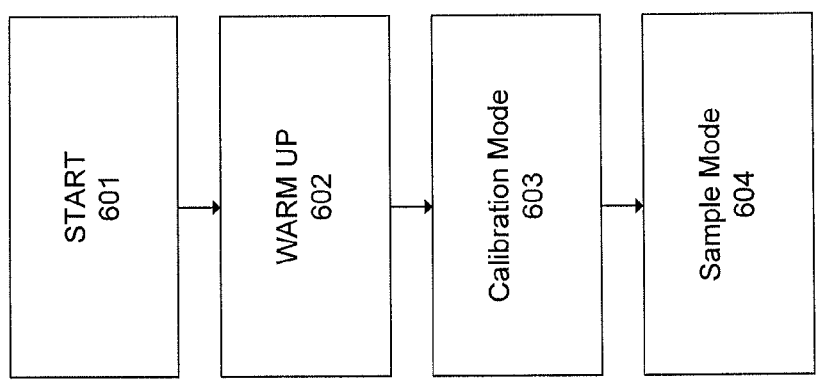
FIG. 6 is a flow diagram of a non-limiting method in accordance with the present disclosure.

In start step 601, a sampling system in accordance with the present disclosure is provided. Before the sampling system takes the sample from a source of sample gas (e.g., engine or vehicle exhaust), it may be fully warmed up to a constant or substantially constant temperature, as depicted in FIG. 6 as warm up step 602. System warm up may be facilitated by enclosing all or a portion of the components of the sampling system in a heated enclosure, such as enclosure 209 described previously. The warm up temperature may be set and/or controlled by one or more temperature controllers, e.g., for the heated enclosure or other components.

Upon achieving a desired warm up temperature, the sampling system may be calibrated in calibration step 603 by inputting a pre-determined reference pressure differential signal to controller 203, or by measuring the reference pressure differential signal from a source of calibration gas. Such calibration may take place in a "calibration mode" that facilitates the measurement or input of the reference pressure differential signal, e.g., by isolating the sampling system from other external inputs. In some embodiments, instruments downstream of the sampling system are isolated from the flow of calibration and/or sample gas, e.g., by a cutoff valve located between system outlet 208 and downstream instrumentation. When the cutoff valve is fully closed, flow to the downstream instrumentation is prevented, and the flow of calibration gas may exit the sampling system through another outlet or a bypass connected to the outlet of the instrumentation downstream of the sampling system.

Measurement of a reference pressure differential signal may be achieved with or without the use of a directional valve, such as solenoid 502 shown in FIG. 5. In embodiments wherein the sampling system is configured to include such a directional valve, calibration of the sampling system may be achieved by actuating the directional valve such that it is connected to a source of calibration gas. With reference to FIG. 5, this can be achieved by actuating solenoid 502 to position b, so as to enable the flow of a calibration gas (e.g., ambient air) to pressure monitor 202. Pressure monitor 202 induces and records a pressure differential in the flow of calibration gas, and outputs a corresponding reference pressure differential signal to controller 203.

In embodiments wherein the sampling system does not include a directional valve such as solenoid 502, calibration may be achieved by connecting the sampling system to a source of calibration gas upstream of pressure monitor 202. Once the reference pressure differential signal is measured, the sampling system may be reconnected to a source of sample gas. This methodology may be particularly useful when the sample flow for the instrumentation downstream of system outlet 208 (e.g., an emissions bench) is stable, because it may not be necessary to recalibrate the sampling system after every measurement.

Regardless of whether the reference pressure differential signal is input or measured, it may be utilized as a set point (reference value) for controller 203. That is, the reference pressure differential signal may be utilized by controller 203 to determine the difference between the pressure differential of a sample gas flow through pressure monitor 202 and the reference pressure differential.

After the reference pressure differential signal has been input to controller 203, the sampling system may take a sample from a source of sample gas, such as the exhaust of an internal combustion engines. At this time, the opening of proportional valve 207 may be adjusted to an initial setting, such as fully open, fully closed, or a predetermined intermediate setting. In some embodiments, proportional valve 207 is set to a fully open position prior to the time at which the sampling system takes a sample from a source of sample gas. In instances where a directional control valve is used, the directional control valve is actuated to facilitate the flow of sample gas to pressure monitor 202. In the example shown in FIG. 5, this would involve actuating solenoid 502 to position a, so as to permit passage of a sample gas flow through solenoid 502 to pressure monitor 202.

In embodiments wherein a pump is coupled upstream of the pressure monitor, as is the case in the non-limiting example of FIG. 5, the pump may be turn on to facilitate the flow of sample gas through the sampling system. As explained above, a pump may be particularly useful when the inlet pressure of the sample gas is low (e.g., below ambient pressure), especially if a pressure regulator is coupled upstream of the pump.

In the example shown in FIG. 5, the sample gas flows into the sampling system via sample inlet 201, through pressure regulator 402, through pump 404, through solenoid 502, through orifice 304 of pressure monitor 202, and ultimately through system outlet 208. System outlet may be connected to various downstream instrumentation, such as an emissions bench.

The pressure monitor 202 introduces a pressure differential in the flow of sample gas, which is recorded and output by pressure monitor 202 as a pressure differential signal to controller 203. In the non-limiting embodiment shown in FIG. 5, the measured pressure differential signal is received at the negative terminal of summer 310. Summer 310 outputs an error signal corresponding to a difference between the measured pressure differential signal and the reference pressure differential signal to PID loop 308. PID loop 308 then outputs a control signal to proportional valve 207, driving proportional valve 207 further open or closed to adjust the flow rate of the sample gas exiting the proportional valve to the desired flow rate, such as the flow rate of the calibration gas used in the measurement of the reference pressure differential signal.

Specifically, and with reference to FIG. 5, when the measured pressure differential over orifice 304 is higher than the set point (i.e., the reference pressure differential signal), PID loop 308 drives proportional valve 207 further closed, thereby adjusting the flow rate of the sample gas to the flow rate of the calibration gas during the measurement of the reference pressure differential signal. When the pressure difference over orifice 304 is lower than the set point, PID loop 308 drives proportional valve 207 further open to achieve the set point. As a result, the flow rate of the sample gas at system outlet 208 is maintained at a constant value that is the same or substantially the same as a desired flow rate, e.g., the flow rate of the calibration gas used in the measurement of the reference pressure differential signal.

After the orifice pressure difference is recorded, the inlet of the orifice is connected to the outlet of the high temperature leak-free vacuum pump. Finally, the PID loop controls the flow into the emission bench at a constant value by adjusting the proportional valve.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sampling system, comprising
    a system inlet for receiving a gaseous sample;
    a pressure regulator coupled to the system inlet;
    a pump coupled downstream of the pressure regulator;
    a pressure monitor configured to receive the gaseous sample downstream of the system inlet;
    a proportional valve coupled downstream of the pressure monitor; and
    a controller coupled to the pressure monitor and the proportional valve;
    wherein:
        the pressure monitor measures a pressure differential of the gaseous sample as it flows through the pressure monitor, and outputs a first pressure differential signal corresponding to a first gas flow rate to the controller;
        the controller compares the first pressure differential signal to a second pressure differential signal, the second pressure differential signal corresponding to a second gas flow rate; and
        the controller drives the proportional valve open or closed so as to adjust the first gas flow rate to the second gas flow rate.

2. The sampling system of claim 1, wherein the pressure monitor comprises at least one of an orifice flow meter, a venturi flow meter, and a nozzle flow meter.

3. The sampling system of claim 2, wherein the pressure monitor comprises at least one pressure transducer.

4. The sampling system of claim 1, wherein the pressure monitor comprises an orifice flow meter, the orifice flow meter comprising at least one orifice.

5. The sampling system of claim 4, wherein the first pressure differential signal is measured across the at least one orifice.

6. The sampling system of claim 1, wherein at least one of the pressure regulator and the pump is configured to output the gaseous sample at the first gas flow rate.

7. The sampling system of claim 6, wherein the pump comprises a vacuum pump.

8. The sampling system of claim 1, further comprising a three-way solenoid upstream of the pressure monitor, the three-way solenoid comprising a first solenoid inlet, a second solenoid inlet, and a solenoid outlet.

9. The sampling system of claim 8, wherein said first solenoid inlet is configured to deliver the gaseous sample to the pressure monitor via the solenoid outlet, and the second solenoid inlet is configured to deliver a calibration gas flow to said pressure monitor via the solenoid outlet.

10. The sampling system of 1, wherein said second pressure differential signal corresponds to a pressure differential of a calibration gas flowing through the pressure monitor.

11. The sampling system of 10, wherein said calibration gas comprises ambient air.

12. The sampling system of claim 1, wherein said system inlet is coupled to a source of motor vehicle exhaust gas.

13. A method, comprising:
    providing a gas sampling system, the gas sampling system comprising:
        a system inlet for receiving a gaseous sample at an inlet pressure;
        a pressure regulator coupled to the system inlet;
        a pump coupled downstream of the pressure regulator;
        a pressure monitor configured to receive the gaseous sample downstream of the system inlet;
        a proportional valve coupled downstream of the pressure monitor; and
        a controller coupled to the pressure monitor and the proportional valve;
    supplying a gaseous sample to the pressure monitor at a first gas flow rate;
    measuring a pressure differential of the gaseous sample as it flows through the pressure monitor;
    providing a first pressure differential signal corresponding to the pressure differential to at least one controller;
    comparing the first pressure differential signal to a second pressure differential signal with said controller, the second pressure differential signal corresponding to a second gas flow rate; and
    outputting a signal from the at least one controller to drive the proportional valve open or closed, thereby adjusting the first gas flow rate to the second gas flow rate.

14. The method of claim 13, wherein the pump comprises a vacuum pump.

15. The method of claim 13, further comprising supplying the gaseous sample to at least one of the pressure regulator and the pump at an inlet pressure, and outputting the gaseous sample to the pressure monitor at the first gas flow rate.

16. The method of claim 15, further comprising outputting the gaseous sample from the pump at the first gas flow rate.

17. The method of claim 14, wherein the inlet pressure ranges from 30 kPa below ambient pressure to 1000 kPa above ambient pressure.

18. The method of claim 14, further comprising:
    coupling the pressure monitor to a source of calibration gas;
    providing a calibration gas flow to the pressure monitor;
    measuring a pressure differential of the calibration gas flow with the pressure monitor; and
    providing the second pressure differential signal to the control system;
    wherein the second pressure differential signal corresponds to the pressure differential of the calibration gas flow.

19. The method of claim 18, wherein the sampling system further comprises a three-way solenoid upstream of the pressure monitor, the three-way solenoid comprising a first solenoid inlet, a second solenoid inlet, and a solenoid outlet, the first solenoid inlet coupled to a source of the gaseous sample, the second solenoid inlet coupled to the source of the calibration gas, the method further comprising:
    placing the gas sampling system in a calibration mode or a sample mode;

when the sample system is in the calibration mode, supplying the calibration gas flow to the pressure monitor via the solenoid outlet; and when the sample system is in the sample mode, supplying the gaseous sample to the pressure monitor via the solenoid outlet.

20. The method of claim 13, wherein said gaseous sample comprises motor vehicle exhaust gas.

\* \* \* \* \*